United States Patent [19]
Armand et al.

[11] Patent Number: 5,530,066
[45] Date of Patent: Jun. 25, 1996

[54] MONOMERS DERIVED FROM PERHALOGENATED SULTONES AND POLYMERS OBTAINED FROM THESE MONOMERS

[75] Inventors: Michel Armand, Saint-Martin D'Uriage; Jean-Yves Sanchez, Saint-Ismier, both of France; Salime Sylla, Bamako, Mali

[73] Assignees: Centre Nationale de la Recherche Scientifique, Paris, France; Hydro Quebec, Montreal, Canada

[21] Appl. No.: 433,014

[22] Filed: May 3, 1995

Related U.S. Application Data

[62] Division of Ser. No. 391,070, Feb. 21, 1995, which is a division of Ser. No. 137,020, Mar. 8, 1994, Pat. No. 5,414,117.

[30] Foreign Application Priority Data

Feb. 21, 1992 [FR] France ................. 92 02027
Feb. 19, 1993 [WO] WIPO ............ PCT/FR93/00167

[51] Int. Cl.$^6$ ................. C08G 75/00; C07C 303/08; C08J 5/20
[52] U.S. Cl. ................. 525/242; 521/28; 528/373; 556/428; 562/828
[58] Field of Search ................. 521/28; 525/242; 528/373; 556/428; 562/828

[56] References Cited

U.S. PATENT DOCUMENTS

| | | | |
|---|---|---|---|
| 4,950,793 | 8/1990 | Souma et al. | 562/826 |
| 5,021,308 | 6/1991 | Armand et al. | 429/194 |
| 5,030,752 | 7/1991 | Souma et al. | 562/828 |
| 5,072,040 | 12/1991 | Armand | 564/82 |
| 5,136,097 | 8/1992 | Armand | 568/28 |
| 5,162,177 | 11/1992 | Armand et al. | 429/194 |

*Primary Examiner*—Shelley A. Dodson
*Attorney, Agent, or Firm*—Oblon, Spivak, McClelland, Maier & Neustadt

[57] ABSTRACT

The invention relates to monomers derived from perhalogenated sultones, to a process for their preparation, to the polymers obtained from the said monomers and to their use for the production of ion-conductive materials.

The monomers are compounds corresponding to the formula A—CFX—SO$_2$Z in which A denotes one group R$^3$—O—CF$_2$— or R$^3$— or R$^1$R$^2$N—CO—; Z denotes F, Cl, —OSi(CH$_3$)$_3$ or an ionic group, Z being other than F when A denotes R$^3$—O—CF$_2$— or R$^3$—; X denotes F, Cl, H or R$_F$, X being R$_F$ when A denotes R$^3$—; the radicals R$^1$, R$^2$ and R$^3$ are chosen from polymerizable nonperfluorinated organic radicals; R$_F$ is chosen from perfluoroalkyl radicals and perfluoroaryl radicals.

The polymers obtained from these monomers can be employed for the production of ion-conductive materials.

3 Claims, No Drawings

MONOMERS DERIVED FROM PERHALOGENATED SULTONES AND POLYMERS OBTAINED FROM THESE MONOMERS

This is a Division of application Ser. No. 08/391,070, filed on Feb. 21, 1995, pending; which is a Divisional of Ser. No. 08/137,020, filed on Mar. 8, 1994, U.S. Pat. No. 5,414,117; which was filed as International Application No. PCT/FR93/00167 on Feb. 19, 1993.

The present invention relates to monomers derived from perhalogenated sultones, to the process for their preparation, to the polymers obtained from said monomers and to their use for the production of ion-conductive materials.

Compounds $ROCF_2CF(CF_3)SO_2F$ are known, in which R is an optionally halogenated alkyl group containing a vinyl double bond, an acetylenic bond, an epoxy group or $(CH_3-CH_2-O)_2P(O)-CH_2-CH_2-$ or $CH_3-CH_2-O-P-F(O)-CH_2-CH_2$ groups, as is a process for their preparation from a cyclic fluorinated sultone (Chen et al., J. of Fluorine Chemistry, 48 (1990) 107—122); Chen et al., J. of Fluorine Chemistry, vol. 46, 1990, p. 21–38; Chen et al., J. of Fluorine Chemistry, vol. 46, 1990, p. 39–56). Compounds in which a $-SO_3M$ group, M being H, Li, Na, $NH_4$ or K, is attached to a radical $R^1R^2-N-C(O)-CH-(CH_2)_n-COOM$, n being 0 or 1, $R^1$ and $R^2$ being alkyl groups, are described in U.S. Pat. No. 4,490,308 (D. W. Fong et al.). EP-A-0124378 (Du Pont De Nemours) describes monomers $CH_2=CH-CF_2-CF_2-OCF_2-CF_2-SO_2F$, copolymers of these monomers with ethylene and the use of these copolymers as electrically insulating materials. Compounds resulting from the reaction of a difluoroiodomethanesulfonyl fluoride with an olefin in the presence of copper, for example n—Bu—CH=CH—$CF_2$—$SO_2F$, Me—$C(CH_2)$—$C(CH_3)_2$—$CF_2SO_2F$ or $CH_2=CH-(CH_2)_2-CH=CH-CF_2SO_2F$, are described in Chem. Abs., vol. 114, 1991, No. 23718b, Huaxue.

European Patent No. 13199 (Armand and Duclot) discloses polymeric electrolytes obtained by dissolving a salt $M^+X^-$ in a solvating polymer containing heteroatoms, $M^+$ denoting $H^+$, a metal cation, an organic cation of the ammonium, amidinium or guanidinium type, X denoting an anion with a delocalized electronic charge, for example $Br^-$, $ClO_4^-$, $R_FSO_3^-$ or $(R_FSO_2)_2N^-$, $R_F$ denoting a perfluoroalkyl or perfluoroaryl group. These polymeric electrolytes have many applications, in particular in the field of electrochemical generators, light-modulating systems (M. Armand et al., EP-87401555), sensors, for example for selective or reference membranes (A. Hammou et al., FR-86.09602). Many investigations have been carried out, in particular to improve the conduction properties of these materials. They have resulted, for example, in the formation of copolymers based on ethylene oxide (M. Armand et al., FR-83.09886) or of networks crosslinked by urethane bridges (H. Ch éradame et al., FR-8007135, U.S. Pat. No. 4,357,401). However, these materials have a common characteristic of exhibiting a mobility of the $X^-$ anion which is, in most cases, greater than that of the $M^+$ cation. This property is a disadvantage, in particular in the case of electrochemical systems in which the electrode reaction involves the $M^+$ cation. The current flow gives rise to the formation of a dissolved salt concentration gradient which increases the resistivity of the electrolyte and can bring about the formation, near the interfaces, of polymer-salt stoichiometric compounds exhibiting an insufficient ionic conductivity.

A number of attempts have been made to synthesize polymers containing anionic groups attached to the macromolecular chain. The ionophores containing alkylsulfonate $RSO_3^-$ groups, carboxylate groups or perfluorocarboxylate $-R_FCO_2^-$ groups [D. J. Bannister et al., Polymer 25, 1291 (1984); E. Tsushida et al., Macromolecules 21, 96 (1988)] are, however, very slightly dissociated in solvating polymers of the polyether type such as polyethylene oxide. The ionic conductivities obtained with such materials are thus very low and do not allow any practical applications to be envisaged.

Furthermore, perfluorosulfonic $-R_FSO_3^-$ groups constitute the ionophore groups of the ion exchange membranes of Nafion® type. Such membranes, as well as the monomers from which they are obtained, are described, for example, in DE-A-3047439 (Asahi Kasei Kogyo KK), DE-A-2461675 (Du Pont De Nemours), U.S. Pat. No. 3,718,627 (W. G. Grot) or in U.S. Pat. No. 3,714,245 (R. Beckerbauer). The crosslinkable part of the monomers and the backbone of the polymers forming the membranes are perfluorinated. These polymers exhibit ionic conductivity only in the presence of polar solvents such as water, alcohols and propylene carbonate; the perfluorinated network of this type of polymer does not actually have any solvating or dissociating character, in contrast to the polyethers.

Polymers $-(CX_2CXR)_n-$ or $-(CXRCXR)_n-$ in which X is H or F and R denotes $-(CX_2)_m-SO_3H$, and their use as electrolyte in fuel cells are described in Chem. Abstr., vol. 117, 1992, No. 27945h Matsushita.

WO-A-9202571 (SRI International) describes ion-conductive polymers bearing grafter anions $-X-Y^-M^+$, it being possible for X to be $CF_2$ or $CFR_F$, it being possible for Y to be $SO_3$ and $M^+$ being a cation. The backbone of the polymers is derived from a linear polymer which has mobile hydrogens. It may be, for example, a backbone of the polyether, polyester, poly(ethylene)amine, polyphosphazene or siloxane type. The polymers may be obtained either by grafting appropriate groups onto any polymer chain which has mobile hydrogens, or by polymerizing monomers containing an oxazoline ring bearing a $-SO_2F$ group.

The objective of the present invention is to provide monomers which make it possible to obtain polymers that are particularly advantageous for the production of cation-conductive materials.

The subject of the present invention is thus perhalogenated monomers.

Another subject thereof is a process for preparing these monomers.

A further subject thereof is the polymers obtained from said monomers.

Finally, a subject thereof is ion-conductive materials containing said polymers.

The monomers of the present invention are compounds corresponding to the general formula (1):

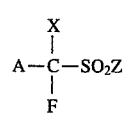

in which:

A denotes one of the groups $R^3$—O—$CF_2$—, $R^3$— or

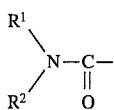

Z denotes F, Cl, —OSi(CH$_3$)$_3$ or an ionic group;
Z being other than F when A denotes $R^3$—O—$CF_2$— or $R^3$—;

X denotes F, Cl, H or $R_F$; X being $R_F$ when A denotes $R^3$—;

the radicals $R^1$, $R^2$ and $R^3$, which are identical or different, are chosen from polymerizable nonperfluorinated organic radicals;

$R_F$ is chosen from perfluoroalkyl radicals and perfluoroaryl radicals.

The ionic groups Z which are particularly preferred are chosen from $1/mM^{m+}[$—O$]^-$, $1/mM^{m+}[$—N—SO$_2$—Q$]^-$, $1/mM^{m+}[$—CH(SO$_2$—Q)$]^-$ and $1/mM^{m+}[$—C(SO$_2$—Q)$_2]^-$, Q denoting —$R_F$ or —CFX—A, with X=$R_F$ when A=$R^3$; $M^{m+}$ denoting an ion of a metal which has the valency m, chosen from alkali metals, alkaline-earth metals, transition metals and the rare earths, or an ammonium ion corresponding to the formula $NH_{(4-j)}R_j^+$, or an amidinium ion corresponding to the formula $RC(NH_{2-j}R_j)_2^+$, or a guanidinium ion corresponding to the formula $C(NH_{2-j}R_j)_3^+$, with j=0, 1 or 2, R being chosen from hydrogen and an alkyl, oxaalkyl or aryl group.

Among the various cations $M^{m+}$, those which correspond to electrode reactions, for example in systems for energy storage, for modulation of electromagnetic radiation, and reference electrodes, are particularly advantageous. In this connection, the ions Li$^+$, Na$^+$, K$^+$, Cs$^+$, NH$_4^+$, Ca$^{++}$, Cu$^{++}$, Zn$^{++}$ and Mg$^{++}$ are particularly preferred.

Among the groups $R_F$ of the perfluoroalkyl type preference is given to perfluoroalkyl radicals containing from 1 to 8 carbon atoms, and more particularly perfluoroalkyl radicals containing from 1 to 4 carbon atoms. The radicals CF$_3$—, C$_2$F$_5$—, n—C$_3$F$_7$— and n—C$_4$F$_9$— may be mentioned.

Among the groups $R_F$ of the perfluoroaryl type preference is given to perfluoroaryl radicals containing from 6 to 8 carbon atoms, for example the perfluorophenyl radical.

The polymerizable nonperfluorinated organic groups $R^1$, $R^2$ and $R^3$ allow polymerization reactions by a radical, anionic, cationic or stereospecific route, or by polycondensation. They may be chosen from those containing double bonds, for example double bonds of the vinyl, allyl, vinylbenzyl or acryloyl type. They may also be chosen from those containing oxirane, oxetane, azetidine or aziridine functional groups. Furthermore, they may be chosen from those containing alcohol, thiol, amine, isocyanate or trialkoxysilane functional groups. They may also be chosen from those containing functional groups allowing an electropolymerization.

The substituent R in the ammonium, amidinium or guanidinium groups is preferably chosen from H, alkyl groups containing from 1 to 20 carbon atoms, oxalkyl groups containing from 1 to 20 carbon atoms or aryl groups containing from 6 to 30 carbon atoms. Methyl, ethyl, propyl, lauryl and methoxyethyl groups are very particularly preferred.

Among the monomers of the present invention very particular preference is given to those corresponding to the general formula (1) in which Z denotes an ionic group. The following classes may be mentioned by way of example:

$1/mM^{m+}[A$—CFX—SO$_3]^-$,
$1/mM^{m+}[A$—CFX—SO$_2$—N—SO$_2$—$R_F]^-$, $1/mM^{m+}[A$—CFX—SO$_2$—CH(SO$_2$—$R_F)]^-$,
$1/mM^{m+}[A$—CFX—SO$_2$—C(SO$_2$—$R_F)_2]^-$,
$1/mM^{m+}[A^1$—CFX$^1$—SO$_2$—N—SO$_2$—CFX$^2$—A$^2]^-$,
$1/mM^{m+}[A^1$—CFX$^1$—SO$_2$—CH(SO$_2$—CFX$^2$—A$^2)]^-$,
$1/mM^{m+}[A^1$—CFX$^1$—SO$_2$—C(SO$_2$—CFX$^2$—A$^2)_2]^-$,
$A^1$ and $A^2$, which are identical or different, being chosen from the groups A mentioned above; $X^1$ and $X^2$, which are identical or different, being chosen from the groups X mentioned above, it being understood that X is $R_F$ if corresponding A is $R^3$.

The following monomeric compounds are particularly advantageous:

(C$_3$H$_5$)$_2$NCOCF$_2$SO$_2$F, K[(C$_3$H$_5$)$_2$NCOCF$_2$SO$_3$],
Na[(C$_3$H$_5$)$_2$NCOCF$_2$SO$_3$], Li[(C$_3$H$_5$)$_2$NCOCF$_2$SO$_3$],
(C$_3$H$_5$)$_2$NCOCF(CF$_3$)SO$_2$F, K[(C$_3$H$_5$)$_2$NCOCF(CF$_3$)SO$_3$],
Na[(C$_3$H$_5$)$_2$NCOCF(CF$_3$)SO$_3$], Li[(C$_3$H$_5$)$_2$NCOCF(CF$_3$)SO$_3$],
Li[H$_2$C=CHCH$_2$O(CF$_2$)$_2$SO$_3$], Li[(C$_3$H$_5$)$_2$NCOCF(CF$_3$)SO$_2$]$_2$N,
Li[H$_2$C=CHCH$_2$O(CF$_2$)$_2$SO$_2$(CF$_3$SO$_2$)$_2$C,
K[CH$_2$OHCHOHCH$_2$O(CF$_2$)$_2$SO$_3$],
Li[(CH$_3$O)$_3$Si(CH$_2$)$_3$N(CH$_3$)COCF(CF$_3$)SO$_3$],
K[H$_2$C=CHCOCF(CF$_3$)SO$_3$],

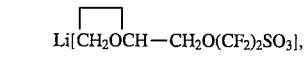

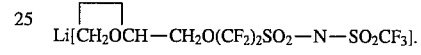

The compounds of the present invention can all be obtained advantageously from a cyclic sultone (2) obtained directly by reaction between sulfur trioxide SO$_3$ and a polyhalogenated ethylene derivative, and converted quantitatively into the fluoride of sulfonylacetic acid (3) by isomerization in the presence of a nucleophilic base. The nucleophilic base catalyzing the isomerization of the cyclic sultone may be chosen from ethers (for example diethyl ether, tetrahydrofuran, the glymes), ionic fluorides and nitrogenous bases (for example pyridines and trialkylamines).

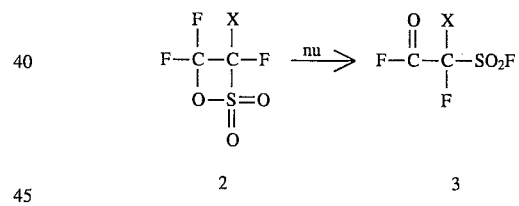

The compounds of the present invention which correspond to the formula (1) in which A denotes $R^1R^2N$—CO— and Z denotes F, referred to hereinafter as compounds (4), are obtained by reaction of the fluoride of sulfonylacetic acid (3) with an amine in the presence of a base, according to the following reaction scheme:

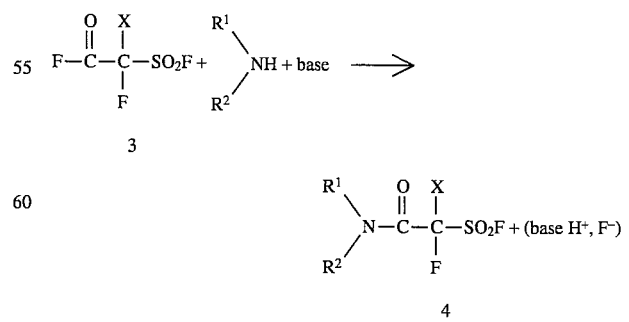

In a preferred embodiment the base which allows the acid HF formed during the reaction to be neutralized is an ion exchange resin of weakly basic type, for example a tertiary amine, and this allows the byproducts of the reaction to be easily separated off merely by filtration. In another embodiment the excess amine $R^1R^2NH$ can be employed as the base.

A compound of the present invention corresponding to the formula (1) in which A denotes $R^1R^2N$—CO— and Z is other than F, referred to hereinafter as compound (5), is obtained by reacting the compound (4) with the appropriate reactant.

Thus, a compound (5a) in which $Z=1/mM^{m+}[-O^-]$ is obtained by reaction of a compound (4) with $1/mM^{m+}OH^-$ or with $1/mM^{m+}[OSi(CH_3)_3]^-$.

A compound (5b) in which Z is Cl is obtained by reaction of a compound (4) with a chloride $1/mM^{m+}Cl^-$, preferably with an alkali or alkaline-earth metal chloride, according to the reaction:

A—CFX—$SO_2F$+$1/mM^{m+}Cl^-$→A—CFX—$SO_2Cl$+$1/mM^{m+}F^-$

A compound (5c) in which Z is —$OSi(CH_3)_3$ is obtained by reaction of the compound (4) with a silylating agent, in particular hexamethyldisiloxane, according to the reaction:

A—CFX—$SO_2F$+$(CH_3)_3SiOSi(CH_3)_3$→A—CFX—$SO_3Si(CH_3)_3$+$FSi(CH_3)_3$

A compound (5d) in which $Z=1/mM^{m+}[-NSO_2Q]^-$ is obtained by reaction of the corresponding compound (4) with $1 mM^{m+}]HNSO_2Q]^-$ in the presence of a nucleophilic base.

A compound (5e) in which $Z=1/mM^{m+}[-CH(SO_2Q]^-$ is obtained by reaction of the corresponding compound (4) with $1/mM^{m+}[H_2C(SO_2Q)]^-$ in the presence of a nucleophilic base.

A compound (5f) in which $Z=1/mM^{m+}[-C(SO_2Q)_2]^-$ is obtained by reaction of the corresponding compound (4) with $1/mM^{m+}[HC(SO_3Q)_2]^-$ in the presence of a nucleophilic base. In the compounds (5d) to (5f) Q denotes A—CFX— or $R_F$—.

The nucleophilic base is preferably chosen from trialkylamines [for example triethylamine, diisopropylethylamine, quinuclidine, 1,4-diazabicyclo[2.2.2]octane (TED)], pyridines (for example pyridine, alkylpyridines, dialkylaminopyridines), imidazoles (for example N-alkylimidazoles, imidazo[1,2-a]pyridine), amidines, for example 1,5-diazabicyclo[4.3.0]-5-nonene (DEN) and 1,8-diazabicyclo [5.4.0[-7-undecene (DBU)], guanidines [for example tetramethylguanidine and 1,3,4,7,8-hexahydro-1-methyl-2H-pyrimido [1,2-a]pyrimidine (HPP)].

The compounds of the present invention corresponding to the formula (1) in which A denotes $R^3O$—$CF_2$—, referred to hereinafter as class (6), are obtained from the fluoride of sulfonylacetic acid (3) by a three-stage process. During a first stage the fluoride of sulfonylacetic acid (3) is reacted with a fluoride M'F; during a second stage the perfluoroalkoxide (7) obtained is brought into contact with a reactant $R^3Y$ to obtain the compound $R^3O$—CF—CFX—$SO_2F$ (8) according to the reaction schemes:

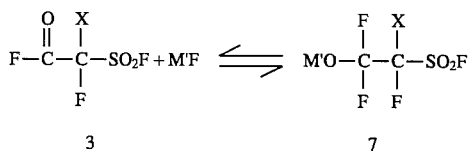

3  7

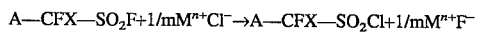

7

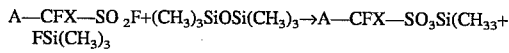

8

Finally, during a third stage the compound (8) is reacted with the appropriate reactant to replace the fluorine in the $SO_2F$ group with Cl, —$OSi(CH_3)_3$, an ionic group chosen from $1/mM^{m+}[-O]^-$, $1/mM^{m+}[-NSO_2 R]^-$, $1/mM^{m+}[-CH(SO_2 R_F)]^-$ or $1/mM^{m+}[-C(SO_2R_F)_2]^-$, by processes similar to those described for obtaining the compounds (5) from a compound (4).

The fluoride M'F is a fluoride of a metal cation or of a weakly polarizing organic cation. Among the appropriate cations there may be mentioned the ions $Ag^+$, $K^+$, $Rb^+$, $Cs^+$, tetraalkylammonium ions, tetraalkylphosphonium ions and tetra(dialkylamino)phosphonium ions.

In the reactant $R^3Y$, Y denotes a leaving group such as Cl, Br, I, an alkylsulfonate, an arylsulfonate or a perfluoroalkylsulfonate.

The compounds of the present invention corresponding to the formula (1) in which A denotes $R^3$—, Z is other than F and X denotes $R_F$, referred to hereinafter as compounds (9), are obtained from the fluoride of sulfonylacetic acid (3) by a three-state process. During a first stage the fluoride of sulfonylacetic acid is treated with water, which results in a hydrolysis followed by a decarboxylation according to the following reaction scheme:

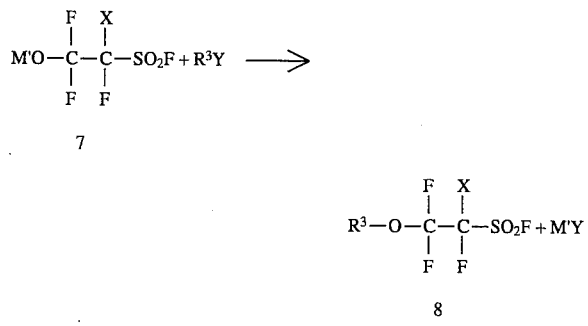

3  10

The compound (10) which is obtained has, on the α carbon, a proton which is acidic in nature, permitting the formation of a carbanion which, during a second stage, gives rise to a nucleophilic substitution reaction in the presence of a base, which makes it possible to obtain the compound (11) according to the following reaction scheme:

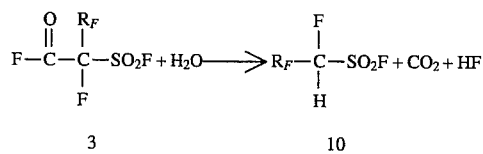

10

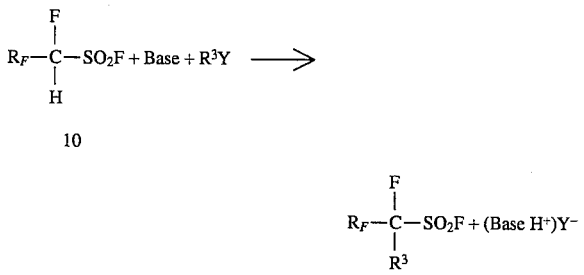

11

The base is preferably chosen from nitrogenous derivatives exhibiting a stearic hindrance preventing the formation of a quaternary ammonium by direct reaction with $R^3Y$.

During a third stage the compound (11) which is obtained is reacted with the appropriate reactant to replace the fluorine in the $SO_2F$ group with Cl, $-OSi(CH_3)_3$, or an ionic group chosen from $1/mM^{M+}[-O]^-$, $1/mM^{m+}[-NSO_2R_F)]^-$, $1/mM^{m+}[-CH(SO_2R_F)]^-$ or $1/mM^{m+}[-C(SO_2R_F)_2]^-$, according to processes which are similar to those described for obtaining the compounds (5) from a compound (4).

When a monomeric compound of the present invention is a symmetrical compound such as $1/mM^{m+}[(A-CFX-SO_2)_2N]^-$, $1/mM^{m+}[(A-CFX-SO_2)_2CH]^-$ or $1/mM^{m+}[(A-CFX-SO_2)_3C]^{3-}$, it may be prepared by direct action of the fluoride of sulfonylacetic acid $A-CFX-SO_2F$, obtained by isomerization of the corresponding cyclic sultone, on the ionic nitrite $Li_3N$ or the ionic carbide $C_3Al_4$ in a polar aprotic solvent, the group A denoting $R^1R^2N-CO-$ or $R^3O-CF_2-$ or $R^3-$.

The monomers of the present invention in which Z denotes an ionic group, which are obtained by one of the processes described above, can, of course, be modified by conventional cation exchange processes, for example with the aid of ion exchange resins, with a view to replacing the cation M with another cation.

When the polymerizable groups existing in the groups $R^1$, $R^2$ and $R^3$ contain functional groups whose reactivity could interfere with reactions for preparing the monomers as described above, the said functional groups can be protected by reactants which are reversibly bound to them.

The monomeric compounds of the present invention can be polymerized by virtue of the polymerizable functional groups present in the groups $R^1$, $R^2$ and $R^3$. The polymers obtained according to the present invention carry functional groups $-SO_2Z$.

According to a first alternative form a linear polymer is obtained in which the network consists of the polymerized groups $R^1$, $R^2$ or $R^3$ and carries grafts which have $-SO_2Z$ ends. This polymer is obtained by homopolymerization of a monomeric compound of the present invention. The monomeric compounds of the present invention can be homopolymerized when the group A contains at least two complementary reactive functional groups. Groups A containing a diallylamino, vinylphenylamino or acrylamidoethylamino group may be mentioned by way of example.

According to a second alternative form the polymers of the present invention are obtained in the form of copolymers by starting with at least one monomer of the present invention and one or more comonomers. At least one of the comonomers is chosen so that it contains a functional group capable of reacting with the polymerizable group of the monomer according to the invention. The comonomers may additionally be chosen as a function of the particular properties which they will impart to the copolymer. In this respect it is also possible to introduce into the copolymer additional monomers which do not react with the monomer of the invention but which are advantageous owing to their properties.

The copolymers can be obtained by two different routes. According to a first route a polymer containing monomeric units of the present invention is obtained by cocrosslinking the monomeric compounds of the present invention with a preexisting homopolymer or copolymer containing functional groups capable of reacting with the functional group carried by at least one of the groups $R^1$, $R^2$ or $R^3$. The macromolecular networks thus obtained consist of a macromolecular network consisting of the preexisting homopolymer or copolymer onto which are grafter the monmeric units according to the invention, containing a group $-SO_2Z$. As example of preexisting polymers there may be mentioned polymers obtained by polymerization of allyl glycidyl ether, optionally in the presence of other monomers such as ethylene oxide or methyl glycidyl ether, butadiene-acrylonitrile copolymers, or a copolymer of α, ω-diaminooligooxyethylene diisocyanate and poly(oxyethylenetriol). According to a second route the monomeric compounds of the present invention may be incorporated into polymers by direct copolymerization with one or more comonomers at least one of which carries functional groups capable of reacting with the functional group carried by at least one of the groups $R^1$, $R^2$ and $R^3$. Among these monomers which are capable of polymerizing with a monomer of the invention there may be mentioned allyl glycidyl ether, epoxyalkenes and glycidyl acrylates; among the non-reactive monomers there may be mentioned ethylene oxide, propylene oxide and methyl glycidyl ether.

In all cases, when the chosen monomer according to the invention is of the symmetrical type, that is to say when the substituent Z contains a group $A-GFX-$, which may be identical with or different from the group $A-CFX-$ originating from the fluoride of the initial acetylsulfonic acid, the copolymers obtained are crosslinked.

When the polymers of the present invention are obtained from monomers according to the invention containing an ionic group Z, they can be treated in conventional manner, for example with the aid of cation exchange resins, to replace a cation $M^{m+}$ with a different cation.

The polymers and the macromolecular networks of the present invention can be employed for the production of ion-conductive materials.

The polymers or the macromolecular networks incorporating monomers according to the present invention are particularly advantageous when Z denotes an ionic group chosen from $1/mM^{m+}[-O]^-$, $1/mM^{m+}[-NSO_2Q]^-$, $1/mM^{m+}[-CH(SO_2Q)]^-$ and $1/mM^{m+}[-C(SO_1Q)_2]^-$, Q denoting $R_F$ or $[R^1R^2NCOCF(X)-]$ or $[R^3OCF_2CF(X)-]$ or $[R^3CF(R_F)-]$. In this case they carry anions grafted onto the macromolecular chain and per se constitute ion-conductive materials without any supplementary addition of salts. The presence of easily dissociable salts can, nevertheless be useful.

when the polymers and the macromolecular networks of the present invention carry a substituent Z which is not an ionic group, an easily dissociable salt must be added thereto during the production of an ion-conductive material.

The ion-conductive materials of the invention, and more especially those in which the anions are bonded to the macromolecular chain, are particularly useful in electrochemical systems in which the electrode reaction involves cations, for example in electrochemical cells incorporating an anode containing lithium. Among these electrochemical systems there may be mentioned lithium electrochemical generators, electrochromic systems or else sensors incorporating selective membranes or reference membranes.

The present invention is described in greater detail in the following examples which are given by way of illustration but without any limitation being implied.

EXAMPLE 1

Perfluoropropanesultone (12) is obtained by addition of hexafluoroprene to sulfur trioxide, and the compound is purified by distillation (b.p.=45° C. at $10^5$ Pa).

50 ml of anhydrous ethyl ether and 4 g of weakly basic ion exchange resin (Amberlyst® A-21) dried beforehand in vacuum at 60° C. are introduced into a round bottom flask equipped with four necks making it possible to fit a dropping funnel, an entry and an exit for dry argon and a mechanical stirrer bearing. The reactor is cooled to −20° C. and 4.6 g of hexafluoropropanesultone are added dropwise. The exothermic isomerization is catalyzed by the basic resin, giving the acid fluoride FCOCF(CF$_3$)SO$_2$F. Stirring is continued for ten minutes after the end of addition of the sultone.

1.9 g of diallylamine are then added very slowly to the above solution so as to be always deficient in relation to the isomerized sultone and to permit only the attack on the most reactive functional group, the carboxylic acid fluoride (—COF). After the end of the addition of diallylamine stirring is continued for 30 min while the reaction mixture returns to ambient temperature. After filtration of the solution to separate off the resin, the ether is evaporated off and the liquid obtained is distilled at reduced pressure on a spinning-band column. The final product (13) is a colorless liquid which is soluble in many organic solvents such as ether, acetone, THF, acetonitrile and pentane.

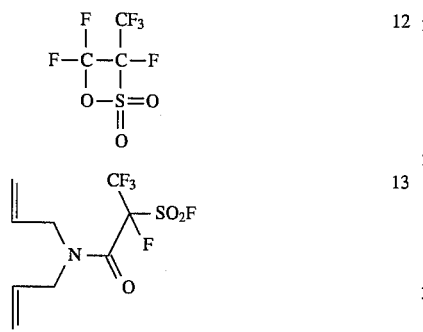

EXAMPLE 2

1.5 g of the sulfonyl fluoride (13) obtained in Example 1 were dissolved in 5 ml of THF and converted into alkali metal slat by the action of 636 mg of potassium trimethylsilanoate dissolved in 10 ml of THF. The reaction was fast and complete at ambient temperature with elimination of gaseous fluorotrimethylsilane (b.p.=16° C.) under the experimental conditions.

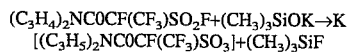

The THF was stripped off, the residue taken up in ether and the salt recovered after filtration and evaporation of the ether. 1.42 g of potassium salt were thus obtained (yield>90%). It is in the form of a weakly hygroscopic white powder which is soluble in water and in many organic solvents, such as THF and acetonitrile.

The sodium salt can be prepared in the same way from sodium trimethylsilanoate.

EXAMPLE 3

600 mg of lithia monohydrate are added to 2 g of the sulfonyl fluoride obtained in Example 1, dissolved in 10 ml of THF. The suspension is stirred at ambient temperature for 48 hours. The complete disappearance of the sulfonyl fluoride is verified by vapor phase chromatography (VPC). The reaction takes place according to the scheme:

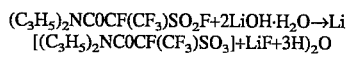

The mixture is next centrifuged and then, after evaporation of the solvent, the residue is taken up in ether and centrifuged; the process is repeated 3 times. The salt is finally precipitated in pentane and dried at 60° C. in vacuum for 48 h before being stored under argon.

EXAMPLE 4

6.6 g of a terpolymer of ethylene oxide, methyl glycidyl ether and allyl glycidyl ether, of mass $\overline{M}_w=2.5\times10^5$, are dissolved in acetonitrile. To the solution thus obtained are added 1% by weight relative to the polymer of benzoyl peroxide and 2.3 g of the ionic monomer from Example 3. A film of polymer-salt complex with a thickness of 40 μm is obtained by casting the solution in a glass ring placed on a poly(tetrafluoroethylene) sheet and evaporating the solvent. The complex can be represented diagrammatically by the following formula:

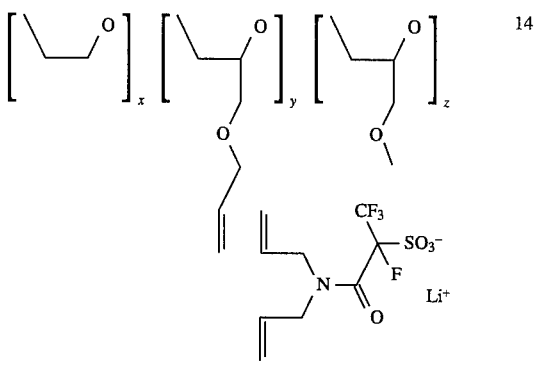

The film is next heated under dry argon atmosphere at 80° C. for 3 h. The double bonds of the allyl groups of the polymer and those of the added salt react with each other after initiation by the peroxide to form a crosslinked frame. The film obtained is washed a number of times with acetone to remove the residual monomer and the oligomers of low molecular weight. Nuclear magnetic resonance confirms the immobility of the anions (measurement using the pulsed field gradient method under $^{19}$F in the salt). The film has excellent mechanical properties and its conductivity is $7\times10^{-5}$ $(\Omega cm)^{-1}$ at 65° C. Its structure can be represented diagrammatically by:

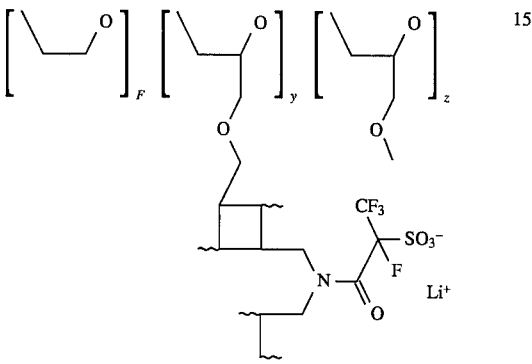

EXAMPLE 5

11 g of methoxy(oligooxyethylene) methacrylate formed by esterification of methoxy(polyethylene glycol) of mass 1000 with methacryloyl chloride are mixed with 50 ml of water and the solution is deoxygenated by bubbling with argon and maintained at 5° C. 200 mg of potassium persulfate $K_2S_2O_8$ used in combination with 260 mg of ferrous sulfate $FeSO_4 \cdot 7H_2O$ are next added while the mixture continues to be stirred, together with 3.1 g of the ionic monomer from Example 2. The polymerization is stopped by adding 200 mg of hydroquinone. The reaction mixture is purified by ultrafiltration, making it possible to remove the molecules (salts, monomers, oligomers) of molecular masses smaller than 10K daltons. The copolymer is next dried in vacuum at 60° C. for several days. Study of its IR spectrum makes it possible to calculate the quantity of salt incorporated into the copolymer. The conductivity of the copolymer is $1 \times 10^{-5}$ $(\Omega cm)^{-1}$ at 53° C.

EXAMPLE 6

A secondary electrochemical generator incorporating polymers according to the present invention was produced. The anode consists of a film of metallic lithium 14 µm in thickness laminated onto an 8-µm polypropylene sheet, metalized with 100 nm of nickel. The electrolyte is the copolymer (15) from Example 4. The positive electrode is a composite material containing 45% by volume of lithium manganite of $LiMn_2O_4$ spinel structure ground into grain of ≈8 µm, 5% v/v of carbon black of Ketjenblack EC-600JD type and 50% v/v of the polymer from Example 5. A pebble mill is employed to obtain a homogeneous dispersion of the constituents of the positive electrode in acetonitrile making it possible, by a spreading technique, to obtain films of 60-µm thickness on a current collector consisting of a polypropylene sheet metallized with nickel, similar to that of the negative electrode. The lamination of the components makes it possible to obtain a flexible generator of 131-µm thickness, characterized by an e.m.f. of 3 V, and a current density of 500 µA/cm² at 70° C. in the case of a voltage of 2.8 V. This system is rechargeable.

EXAMPLE 7

Glycidyloxytetrafluoroethanesulfonyl fluoride of formula:

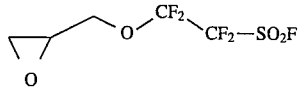     16 is prepared by the method of Gard et al. [J. Fluorine Chemistry 46 21 (1990); ibidem 46 39 (1990); ibidem 48 107 (1990)] by the action of epibromohydrin on the product of addition of silver fluoride AgF to isomerized tetrafluoroethanesultone in diglym. After removal of the silver bromide formed, the product is distilled (b.p.: 115° C. at $1.2 \times 10^4$ Pa). 2.59 g of glycidyloxytetrafluoroethanesulfonyl fluoride (16) are converted into the corresponding potassium salt:

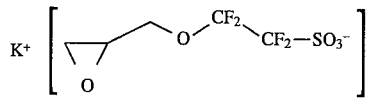     17 by the action of a stoichiometric quantity of potassium trimethylsilanoate in THF. The salt is purified by recrystallization from water.

A reactor connected to a vacuum manifold is charged with 440 mg of potassium tert-butoxide and 2.9 g of the potassium salt (17). The system is degassed in vacuum and 25 g of THF, 13.5 g of ethylene oxide and 1.15 g of allyl glycidyl ether, all distilled over sodium mirrors, are allowed to enter the reactor. The polymerization is performed at 80° C. for 8 hours. The copolymer is precipitated in hexane and purified by dissolving in 50 ml of acetone and precipitating in ethyl ether. This operation is repeated six times; in the first three operations 4 g of lithium trifluoromethanesulfonate are dissolved in acetone, allowing the potassium ions in the polymer to exchange with the lithium ions. The polymer obtained is dried in vacuum. Its conductivity at 25° C. is $2.2 \times 10^{-6}$ $(\Omega cm)^{-1}$. This polymer contains the units:

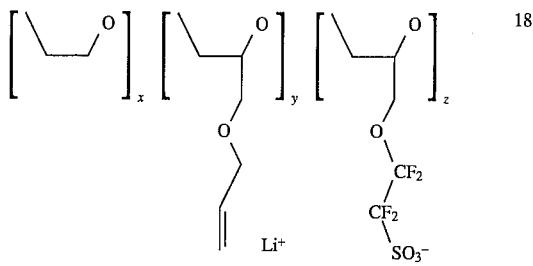     18

A crosslinked film which has good mechanical properties can be obtained by adding 0.5% of benzoyl peroxide and heating to 80° C. under an argon atmosphere for 24 hours. The ionic conductivity of this material is $1 \times 10^{-5}$ $(\Omega cm)^{-1}$ at 41° C.

EXAMPLE 8

Allyloxytetrafluoroethanesulfonyl fluoride of formula:

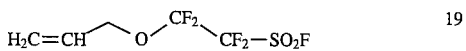     19 is prepared by a method similar to that of Example 7, epibromohydrin being replaced with allyl bromide. The product is purified by distillation (b.p.: 121° C. at $2.2 \times 10^4$ Pa). The corresponding lithium derivative is obtained by the action of lithium hydroxide in methanol, filtering and drying.

4 g of a copolymer of ethylene oxide (90%) and allyl glycidyl ether (10%) are dissolved in 30 ml of acetonitrile and 800 mg of the lithium salt as prepared and 30 mg of benzoyl peroxide are added. The solution is cast to form a film of 40-µm thickness after evaporation. This material is heated to 80° C. under an argon atmosphere for 8 hours, and this allows a cocrosslinking of the salt and of the polymer which have the reactive double bonds whose opening is initiated by the free radicals originating from the decomposition of benzoyl peroxide. The polymer network obtained is washed in four successive baths of acetone to remove the unreacted salt and traces of oligomers. After drying, the film has a conductivity of $10^{-5}$ $(\Omega cm)^{-1}$ at 40° C.

EXAMPLE 9

6.1 g of the sulfonyl fluoride prepared in Example 1 are diluted in 30 ml of anhydrous THF, to which 350 mg of lithium nitride $Li_3N$ are added. The mixture is kept stirred for 48 hours at ordinary temperature. After filtration and evaporation of the solvent 5.5 g of the lithium sulfonimide salt:

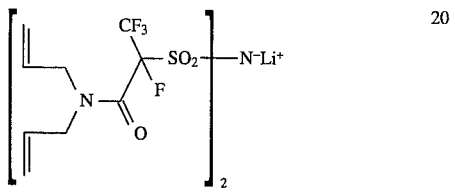     20 are obtained.

This salt is incorporated by cocrosslinking into an ionic polymer similar to that of Example 4. A network containing 17% by weight of bound salt (200 has a conductivity of $3\times10^{-5}$ $(\Omega cm)^{-1}$ at 35° C.

EXAMPLE 10

2.4 g of allyloxytetrafluoroethanesulfonyl fluoride prepared according to Example 8 are dissolved in a mixture of acetonitrile (20 ml) and pyridine (10 ml), both anhydrous, and the solution is treated with 3.02 g of sodium salt of bis(trifluoromethanesulfonyl) methane to which 150 μl of triethylamine and 50 mg of dimethylaminopyridine are added, according to the reaction scheme:

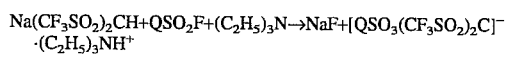

Q here denoting the allyloxytetrafluoroethane group.

The corresponding lithium derivative is obtained by the action of 1.2 g of lithium phosphate in suspension in methanol, filtering and drying.

In a manner similar to that of the example 8.4 g of a copolymer of ethylene oxide (90%) and allyl glycidyl ether (10%) are dissolved in 30 ml of acetonitrile and 1.2 g of the lithium salt as prepared and 40 mg of benzoyl peroxide are added. The solution is cast to form a film of 35-μm thickness after evaporation. This material is heated to 80° C. under an argon atmosphere for 8 hours, to obtain a cocrosslinking of the salt and of the polymer. The polymer network obtained is washed in four successive acetone baths to remove the unreacted salt and traces of oligomers. After drying, the film has a conductivity of $3\times10^{-5}$ $(\Omega cm)^{-1}$ at 40° C.

EXAMPLE 11

2.59 g of glycidyloxytetrafluoroethanesulfonyl fluoride from Example 7 are converted into the potassium salt of 2,2-dihydroxypropyloxytetrafluoroethanesulfonic acid by treatment with 22 ml of a 1M solution of potassium hydroxide at 80° C. for 1 hour. The pH is adjusted to 7 with the aid of a 1M sulfuric acid solution and the water is stripped off with the aid of a rotary evaporator. The solid obtained is extracted with 25 ml of anhydrous ethanol and the insoluble potassium sulfate is removed by filtration. After drying, 2.4 g of the salt of structure:

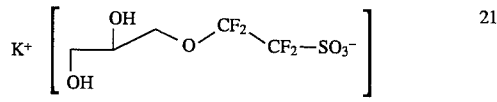

are obtained.

12.7 g of α,ω-diaminooligooxyethylene (Jeffamine® ED600, marketed by Texaco) are treated with 1.96 g of bis(trichloromethyl carbonate) (triphosgene) in the presence of 5 g of basic Amberlyst® A-21 resin, marketed by Rohm & Haas, to form the corresponding diisocyanate; 6.8 g of this compound, 8.8 g of poly(oxyethylene triol) of mass 2000 (marketed by Denko Kagaku), 926 mg of the salt (21) and 40 mg of 4-dimethylaminopyridine are mixed in 10 ml of dichloromethane and cast between two glass sheets separated by a seal of 1-mm thickness. The polycondensation takes place in 48 hours, catalyzed by dimethylaminopyridine. The membrane is demolded and extracted with acetone to remove the unreacted salt and traces of oligomers. The operation is repeated four times. After drying, the membrane has a thickness of 400 μm and a conductivity of $8\times10^{-6}$ $(\Omega cm)^{-1}$ at 25° C. This membrane has excellent mechanical properties and can be employed in modulable optical transmission devices, particularly employing Prussian blue $K[Fe_2(CN)_6]$ as electrochromic material.

EXAMPLE 12

2.44 g of the sodium salt from Example 10 are dissolved in 10 ml of water and treated with 2.7 mg of tetrapropylammonium bromide. The precipitate of tetrapropylammonium allyloxytetrafluoroethanesulfonate is recrystallized from hot water.

5 g of copolymer of butadiene (70 mol %) and acrylonitrile (30 mol %) are dissolved in acetone. 800 mg of the ammonium salt prepared above and 100 mg of benzoyl peroxide are added to the homogeneous solution. The solution is cast to form a film of 35-μm thickness after evaporation. This material is heated to 80° C. under an argon atmosphere for 8 hours to obtain a cocrosslinking of the salt and of the polymer. A material is obtained whose mechanical properties are comparable with those of butadiene-acrylonitrile elastomer without addition of tetrapropylammonium allyloxytetrafluoroethanesulfonate. The material including the monomer of the invention has a conductivity of $3\times10^{-7}$ $(\Omega cm)^{-1}$ at ambient temperature and good antistatic properties.

EXAMPLE 13

2.3 g of anhydrous lithium phosphate $Li_3PO_4$ are added to 2.27 g of N-methylaminopropyltrimethoxysilane in solution in 15 ml of anhydrous ethylether maintained at 0° C. 2.3 g of perfluuoropropane sultone are added dropwise with a dropping funnel, followed by 1 ml of anhydrous pyridine. The mixture is stirred under argon for 24 hours while the temperature is allowed to return to the ambient. The suspension is filtered and evaporated. The lithium salt:

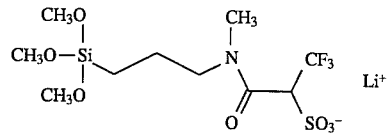

is obtained.

1.5 g of isocyanatopropyltrimethoxysilane are dissolved in 10 ml of anhydrous THF and 2.33 g of O,O'-bis(2-aminopropyl)polyethylene glycol 800 (Jeffamine® ED 900, marketed by Texaco) are added. After reaction of the isocyanate bonds with the —$NH_2$ end groups of the oligomer (24 hours), forming urea bonds, 400 mg of the lithium salt prepared above are added and dissolved; THF is removed in a rotary evaporator. An ion-conductive copolymer is obtained by condensation-hydrolysis of this mixture of monomers. To do this, 10 ml of methanol containing 0.5 ml of water are added. The solution is next cast in a PTFE mold and the polycondensation is performed in an oven at 60° C. for 12 days. A transparent and flexible material is thus obtained which nevertheless has a high scratch resistance. Its ionic conductivity is $1.5\times10^{-6}$ $(\Omega cm)^{-1}$ at 25° C. This organosilicon polymer can be dissolved in water and deposited as a thin layer on glass, to which it exhibits a good adhesiveness, to form an electrochromic windowpane.

EXAMPLE 14

23 g of isomerized perfluoropropylene sultone of Example 1 are added dropwise to 100 ml of water maintained at 1° C. The reaction is accompanied by a release of carbon dioxide. The two-phase mixture is adjusted to a pH of approximately 5 by adding sodium bicarbonate. After separation of the supernatant aqueous phase the compound obtained is distilled and 16 g of $FC(CF_3)HSO_2F$ are obtained. 9.2 g of this compound are dissolved in 60 ml of anhydrous ethylether, and 5 ml of pyridine and 5 ml of triethylamine are added thereto. 4.5 ml of acryloyl chloride are added dropwise. The pyridinium hydrochloride precipitate formed is removed by centrifuging and ether is stripped off with the aid of a rotary evaporator. The compound obtained is distilled and then treated with a stoichiometric quantity of lithium trimethylsilanoate in THF. The structure of the monomer-salt thus obtained is denoted by:

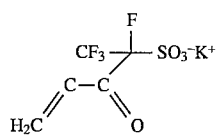

23

This compound has an active double bond capable of homopolymerizing or of copolymerizing to form polyelectrolytes.

EXAMPLE 15

A solvating copolymer is prepared by condensation of glyoxal and of O,O'-bis(2-aminopropyl)polyethylene glycol 500 (Jeffamine® ED600) in the presence of acetic acid. The Schiff polybase thus obtained is hydrogenated with the boron-trimethylamine hydride complex to give a block copolymer containing the blocks:

$(C_2H_4O)_{m11}[C_2H_4N(H)C_2H_4N(H)](C_2H_4O)_{m11}$.

The polymer is purified by ultrafiltration (cutoff at 5K daltons). Its structure is represented diagrammatically by

24

2.3 go of hexafluoropropanesultone are added dropwise to 2 g of weakly basic ion exchange resin (Amberlyst® A-21) dried beforehand in vacuum at 60° C., suspended in 40 ml of anhydrous acetonitrile maintained at −10° C. After isomerization, 10 g of the polymer dried in vacuum at 80° C. and dissolved in 60 ml of anhydrous acetonitrile are added using a dropping funnel, followed by 1.2 g of lithium trimethylsilanoate in solution in THF. The solution obtained is filtered and the polymer is precipitated with ether and then purified by 3 successive dissolutions in acetone followed by precipitations in ether. The material obtained can be denoted by the following structure:

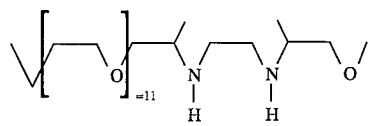

25

The ionic conductivity of the polymer obtained is $1.5 \times 10^{-5}$ $(\Omega cm)^{-1}$ at 25° C. It is soluble in water and in aprotic polar solvents such as acetonitrile, acetone and dimethylformamide.

EXAMPLE 16

Chlorotrifluoroethane sultone is prepared by the action of chlorotrifluoroethylene on sulfuric anhydride. After isomerization, the acid fluoride $FCOC(Cl)FSO_2F$ is obtained, which is treated with diallylamine in the conditions of Example 1. Reaction with lithium hydroxide in ethanol produces $Li[(C_3H_5)_2NCOCF(Cl)SO_3]$. A poly(methoxyethoxyethoxyphosphazene) is prepared by an alternative form of the process described by H. R. Allcock et al., Macromolecules 19, 1508 (1986), replacing 5 mol % of the methoxyethoxyethanol groups with allyl alcohol during the reaction of substitution of the chlorine atoms in poly(dichlorophosphazene). This solvent-polymer then contains solvating groups and allyl units allowing crosslinking. The polymer obtained can be denoted by:

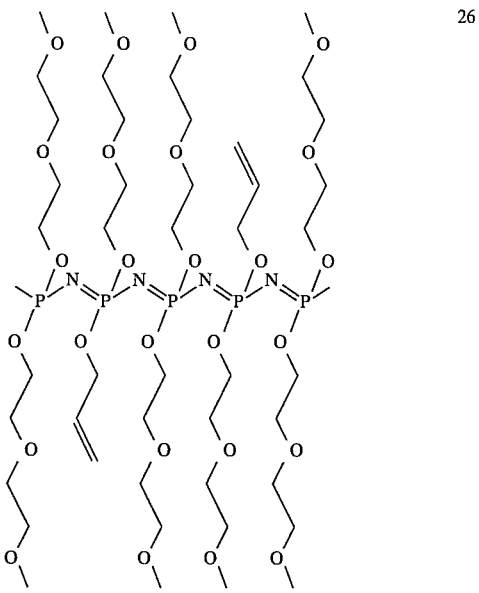

26

5 g of this polymer, 800 mg of the lithium salt prepared above and 150 mg of benzoyl peroxide are dissolved together in acetone and the solvent is evaporated off to leave a film of 37-μm thickness. After treatment at 80° C. under argon for 2 h an elastic membrane is obtained which has a conductivity of $1.5 \times 10^{-5}$ $(\Omega cm)^{-1}$ at 30 ° C.

EXAMPLE 17

3.5 g of the salt from Example 3 are dissolved in 30 ml of water and 100 mg of azobis(cyanovaleric) acid are added. The solution is degassed by bubbling with argon and heated to 80° C. for 4 h. The polymer is precipitated with dioxane and dried in primary vacuum. A monomer of N-oligooxyethylenepyrrole type is prepared by reaction of Jeffamine® M-100 with dimethoxytetrahydrofuran in the presence of acetic acid. 900 mg of the ionic polymer prepared above and 1 g of the substituted pyrrole are dissolved in an electrochemical cell containing 50 ml of acetonitrile. A polymerization using anodic oxidation is performed at +0.95 V relative to the $Hg/Hg_2Cl_2$ reference electrode corresponding to the flow of 220 Cb. The work electrode becomes coated with a black-colored flexible film containing the doped polypyrrole in cationic form, the charges being compensated by those of the anions from the ionic polymer. This material has a mixed, ionic and electronic conductivity and electrochromic properties.

We claim:

1. A macromolecular network obtained by cocrosslinking of a monomer corresponding to the following formula (1)

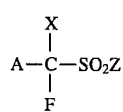

wherein:

A denotes one of the groups $R^3$—O—$CF_2$—, $R^3$— or

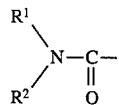

Z denotes F, Cl, —$OSi(CH_3)_3$ or an ionic group:
Z being other than F when A denotes $R^3$—O—$CF_2$— or $R^3$—;

X denotes F, Cl, H or $R_F$; X being $R_F$ when A denotes $R^3$—;

wherein the radicals $R^1$, $R^2$ and $R^3$, which may be identical or different, are chosen from polymerizable nonperfluorinated organic radicals; and $R_F$ is a member selected from the group consisting of perfluoroalkyl radicals and perfluoroaryl radicals;

with a preexisting polymer selected from the group consisting of allyl glycidyl ether homopolymers, copolymers of allyl glycidyl ether with ethylene oxide, copolymers of allyl glycidyl ether with methyl glycidyl ether, butadiene-acrylonitrile copolymers and copolymers of α, ω-diaminooligooxyethylene diisocyanate with poly(oxyethylenetriol);

or copolymerizing said monomer of formula (1) with one or more comonomers selected from the group consisting of allyl glycidyl ether, epoxyalkenes and glycidyl acrylates.

2. An ion-conductive material containing a macromolecular network according to claim 1.

3. A macromolecular network obtained by cocrosslinking of a monomer corresponding to the following formula (1)

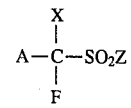

wherein:

A denotes one of the groups $R^3$—O—$CF_2$—, $R^3$— or

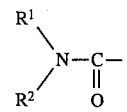

Z denotes F, Cl, —$OSi(CH_3)_3$ or an ionic group:
Z being other than F when A denotes $R^3$—O—$CF_2$— or $R^3$—;

X denotes F, Cl, H or $R_F$; X being $R_F$ when A denotes $R^3$—;

wherein the radicals $R^1$, $R^2$ and $R^3$, which may be identical or different, are chosen from polymerizable nonperfluorinated organic radicals; and $R_F$ is a member selected from the group consisting of perfluoroalkyl radicals and perfluoroaryl radicals;

with a preexisting polymer containing functional groups capable of reacting with a functional group present on at least one of $R^1$, $R^2$ or $R^3$.

* * * * *